United States Patent
Reyes, III et al.

(10) Patent No.: US 9,804,039 B2
(45) Date of Patent: Oct. 31, 2017

(54) SYSTEM AND METHOD FOR POSITION MONITORING USING ULTRASONIC SENSOR

(71) Applicant: Cameron International Corporation, Houston, TX (US)

(72) Inventors: Salvador Reyes, III, Houston, TX (US); Emanuel Gottlieb, St. Clair, PA (US); Donald Augenstein, Pittsburgh, PA (US); Donald Coonrod, Katy, TX (US)

(73) Assignee: Cameron International Corporation, Houston, TX (US)

( * ) Notice: Subject to any disclaimer, the term of this patent is extended or adjusted under 35 U.S.C. 154(b) by 263 days.

(21) Appl. No.: 14/330,311

(22) Filed: Jul. 14, 2014

(65) Prior Publication Data

US 2015/0007651 A1   Jan. 8, 2015

Related U.S. Application Data (63) Continuation-in-part of application No. 13/457,871, filed on Apr. 27, 2012, now Pat. No. 9,187,974.

(51) Int. Cl.
*G01N 29/22* (2006.01)
*G01L 1/00* (2006.01)
*E21B 34/16* (2006.01)

(52) U.S. Cl.
CPC ............... *G01L 1/00* (2013.01); *E21B 34/16* (2013.01); *G01N 29/227* (2013.01);
(Continued)

(58) Field of Classification Search
CPC ......... G01N 2291/01; G01N 2291/022; G01N 2291/102; G01N 29/227; G01B 21/16
See application file for complete search history.

(56) References Cited

U.S. PATENT DOCUMENTS 2,802,196 A   8/1957   Fry et al.
3,510,698 A   5/1970   Massa
(Continued)

OTHER PUBLICATIONS

International Search Report and Written Opinion of PCT Application No. PCT/US2015/039482 dated Sep. 21, 2015: pp. 1-17.
(Continued)

*Primary Examiner* — Natalie Huls
(74) *Attorney, Agent, or Firm* — Chamberlain Hrdlicka (57) ABSTRACT

A system for determining the position of a piston in a subsea accumulator, comprising: a sensor module comprising: a housing; an ultrasonic transducer facing the piston and configured to transmit an ultrasonic pulse through a fluid medium toward a surface of the piston; a pressure sensor configured to; and a temperature sensor; a control connector coupled to the sensor module capable of providing hardware and software functions to measure transit time of the ultrasonic signal from the ultrasonic transducer to the surface of the piston, comprising electronics for controlling the ultrasonic transducer, pressure sensor and temperature sensor; wherein the transit times of the ultrasonic signals across the fluid medium are measured and combined with a computed velocity of sound as a function of temperature/pressure to determine the distance between the ultrasonic transducer and the surface of the piston.

18 Claims, 6 Drawing Sheets

(52) U.S. Cl.
CPC ... *G01N 2291/01* (2013.01); *G01N 2291/022* (2013.01); *G01N 2291/102* (2013.01)

(56) References Cited

U.S. PATENT DOCUMENTS

| | | | |
|---|---|---|---|
| 3,952,216 | A | 4/1976 | Madison et al. |
| 4,543,649 | A * | 9/1985 | Head ................ B60G 17/01933 |
| | | | 367/902 |
| 4,922,423 | A | 5/1990 | Koomey et al. |
| 4,938,066 | A | 7/1990 | Dorr |
| 5,025,708 | A | 6/1991 | Smith et al. |
| 5,164,548 | A | 11/1992 | Angehrn |
| 5,407,172 | A | 4/1995 | Young et al. |
| 5,552,222 | A | 9/1996 | Bolon et al. |
| 5,727,442 | A | 3/1998 | Wimmer |
| 6,037,703 | A | 3/2000 | Kambe et al. |
| 6,446,494 | B2 | 9/2002 | Hastings et al. |
| 6,478,087 | B2 | 11/2002 | Allen |
| 6,578,421 | B1 | 6/2003 | Ishikawa et al. |
| 6,675,111 | B2 | 1/2004 | Komatsu et al. |
| 6,708,570 | B2 | 3/2004 | Matsushima et al. |
| 6,860,327 | B2 | 3/2005 | George |
| 7,300,033 | B1 | 11/2007 | Whitby et al. |
| 7,832,706 | B2 | 11/2010 | Judge |
| 7,836,780 | B2 | 11/2010 | Garnett et al. |
| 8,408,049 | B2 | 4/2013 | Hurmuzlu et al. |
| 8,616,062 | B2 | 12/2013 | Kono et al. |
| 2001/0022756 | A1 | 9/2001 | Nagai et al. |
| 2007/0229303 | A1 * | 10/2007 | Collier ................ G01F 23/0015 |
| | | | 340/850 |
| 2009/0268553 | A1 | 10/2009 | Ecker et al. |
| 2010/0154560 | A1 | 6/2010 | Mueller et al. |
| 2012/0000646 | A1 | 1/2012 | Liotta et al. |
| 2012/0234625 | A1 * | 9/2012 | Laugharn, Jr. ......... G10K 11/28 |
| | | | 181/140 |
| 2012/0305258 | A1 * | 12/2012 | Baugh .................... E21B 43/01 |
| | | | 166/344 |
| 2013/0262010 | A1 * | 10/2013 | Reuter .................. G01B 21/16 |
| | | | 702/94 |
| 2013/0276439 | A1 * | 10/2013 | Edmonson ............. F15B 15/00 |
| | | | 60/327 |
| 2013/0283917 | A1 | 10/2013 | Coonrod et al. |
| 2013/0283919 | A1 | 10/2013 | Coonrod et al. |
| 2014/0123746 | A1 | 5/2014 | Jaffrey et al. |

OTHER PUBLICATIONS

RTD Sensors (Resistance Temperature Detector: Theory and Standards), webpage retrieved from an internet archive as having existed on Jul. 1, 2011 (retrieved on Apr. 13, 2015, from web.archive.org/web/20110701021505/http://www.thermometricscorp.com/rtdsensors.html), pp. 1-5.
International Search Report and Written Opinion for PCT/US2013/037836, dated Jul. 10, 2013.
International Search Report and Written Opinion for PCT/US2013/037828, dated Aug. 20, 2013.

* cited by examiner

SYSTEM AND METHOD FOR POSITION MONITORING USING ULTRASONIC SENSOR

This application is a continuation-in-part of U.S. application Ser. No. 13/457,871, filed Apr. 27, 2012.

BACKGROUND

This section is intended to introduce the reader to various aspects of art that may be related to various aspects of the presently described embodiments. This discussion is believed to be helpful in providing the reader with background information to facilitate a better understanding of the various aspects of the present embodiments. Accordingly, it should be understood that these statements are to be read in this light, and not as admissions of prior art.

In most offshore drilling operations, a wellhead at the sea floor is positioned at the upper end of the subterranean wellbore lined with casing, a blowout preventer ("BOP") stack is mounted to the wellhead and a lower marine riser package ("LMRP") is mounted to the BOP stack. The upper end of the LMRP typically includes a flex joint coupled to the lower end of a drilling riser that extends upward to a drilling vessel at the sea surface. A drill string is hung from the drilling vessel through the drilling riser, the LMRP, the BOP stack and the wellhead into the wellbore.

During drilling operations, drilling fluid, or mud, is pumped from the sea surface down the drill string, and returns up the annulus around the drill string. In the event of a rapid invasion of formation fluid into the annulus, commonly known as a "kick," the BOP stack and/or LMRP may actuate to help seal the annulus and control the fluid pressure in the wellbore. In particular, the BOP stack and the LMRP include closure members, or cavities, designed to help seal the wellbore and prevent the release of high-pressure formation fluids from the wellbore. Thus, the BOP stack and LMRP function as pressure control devices.

For most subsea drilling operations, hydraulic fluid for operating the BOP stack and the LMRP is provided using a common control system physically located on the surface drilling vessel. However, the common control system may become inoperable, resulting in a loss of the ability to operate the BOP stack. As a backup, or even possibly a primary means of operation, hydraulic fluid accumulators are filled with hydraulic fluid under pressure. The amount and size of the accumulators depends on the anticipated operation specifications for the well equipment.

An example of an accumulator includes a piston accumulator, which includes a hydraulic fluid section and a gas section separated by a piston movable within the accumulator. The hydraulic fluid is placed into the fluid section of the accumulator and pressurized by injecting gas (typically inert gas, e.g., nitrogen) into the gas section. The fluid section is connected to a hydraulic circuit so that the hydraulic fluid may be used to operate the well equipment. As the fluid is discharged, the piston moves within the accumulator under pressure from the gas to maintain pressure on the remaining hydraulic fluid until full discharge.

The ability or capacity of the accumulator to operate a piece of equipment depends on the amount of hydraulic fluid in the accumulator and the pressure of the gas. Thus, there is a need to know the volume of the hydraulic fluid remaining in an accumulator so that the capacity of the accumulator to operate well equipment may be determined and control of the well equipment may be managed. Measuring the volume of hydraulic fluid in the accumulator over time can also help identify if there is a leak in the accumulator or hydraulic circuit or on the gas side of the piston.

Currently, the capacity of an accumulator to power equipment is determined by measuring the pressure in the hydraulic circuit downstream of the accumulator. However, pressure is not an indicator of the overall capacity of an accumulator to operate equipment because the volume of hydraulic fluid remaining in the accumulator is not known. Also, accumulators are typically arranged in banks of multiple accumulators all connected to a common hydraulic circuit, therefore, the downstream pressure measurement is only an indication of the overall pressure in the bank, not per individual accumulator.

A possible way of determining the volume of hydraulic fluid remaining in the accumulator is to use a linear position sensor such as a cable-extension transducer or linear potentiometer that attaches inside the accumulator to measure the movement of the internal piston. However, these electrical components may fail and because the discharge of hydraulic fluid may be abrupt, the sensors may not be able to sample fast enough to obtain an accurate measurement.

Another method of determining the volume of hydraulic fluid is through the use of physical position indicators that extend from the accumulator. These indicators only offer visual feedback though and are insufficient for remote monitoring and pose a significant challenge to maintaining the integrity of the necessary mechanical seals under full operating pressures.

Through-the-wall sensors (e.g., Hall effect sensors) have also been considered. However, the thickness and specifications of an accumulator wall is such that these types of sensors are not always able to penetrate the material.

SUMMARY

Certain aspects of some embodiments disclosed herein are set forth below. It should be understood that these aspects are presented merely to provide the reader with a brief summary of certain forms the invention might take and that these aspects are not intended to limit the scope of the invention. Indeed, the invention may encompass a variety of aspects that may not be set forth below.

In accordance with the invention, a system for determining the location of a movable element within a container is provided in which an ultrasonic position sensing system is used to monitor the position of the movable element. In one embodiment, the position sensing system includes an ultrasonic sensor and control connector that measures and computes the position of the movable element relative to the position of the sensor. To determine the movable element position, an ultrasonic transducer in the accumulator directs an ultrasonic pulse toward a surface of the movable element. When the pulse is reflected off the surface, a corresponding echo is received by sensor module, and converted back into an electronic signal by the control connector. The control connector determines several parameters to compute the position of the movable element, including the velocity of the pulse as a function of temperature and pressure and a fluid transit time of the ultrasonic pulse. Thus, once travel time and velocity are known, the system is able to determine the distance traveled by the ultrasonic pulse, which corresponds to the position of the movable element within the accumulator and, accordingly, the level of hydraulic fluid remaining in the accumulator.

This summary is provided to introduce a selection of concepts that are further described below in the detailed description. This summary is not intended to identify key or essential features of the claimed subject matter, nor is it intended to be used as an aid in limiting the scope of the claimed subject matter.

DRAWINGS

For a detailed description of the preferred embodiments of the invention, reference will now be made to the accompanying drawings in which.

DETAILED DESCRIPTION

The following discussion is directed to various embodiments of the invention. The drawing figures are not necessarily to scale. Certain features of the embodiments may be shown exaggerated in scale or in somewhat schematic form and some details of conventional elements may not be shown in the interest of clarity and conciseness. Although one or more of these embodiments may be preferred, the embodiments disclosed should not be interpreted, or otherwise used, as limiting the scope of the disclosure, including the claims. It is to be fully recognized that the different teachings of the embodiments discussed below may be employed separately or in any suitable combination to produce the desired results. In addition, one skilled in the art will understand that the following description has broad application, and the discussion of any embodiment is meant only to be exemplary of that embodiment, and not intended to intimate that the scope of the disclosure, including the claims, is limited to that embodiment.

Certain terms are used throughout the following description and claims to refer to particular features or components. As one skilled in the art will appreciate, different persons may refer to the same feature or component by different names. This document does not intend to distinguish between components or features that differ in name but not function. The drawing figures are not necessarily to scale. Certain features and components herein may be shown exaggerated in scale or in somewhat schematic form and some details of conventional elements may not be shown in interest of clarity and conciseness.

In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection, or through an indirect connection via other devices, components, and connections. In addition, as used herein, the terms "axial" and "axially" generally mean along or parallel to a central axis (e.g., central axis of a body or a port), while the terms "radial" and "radially" generally mean perpendicular to the central axis. For instance, an axial distance refers to a distance measured along or parallel to the central axis, and a radial distance means a distance measured perpendicular to the central axis.

Figure 1:
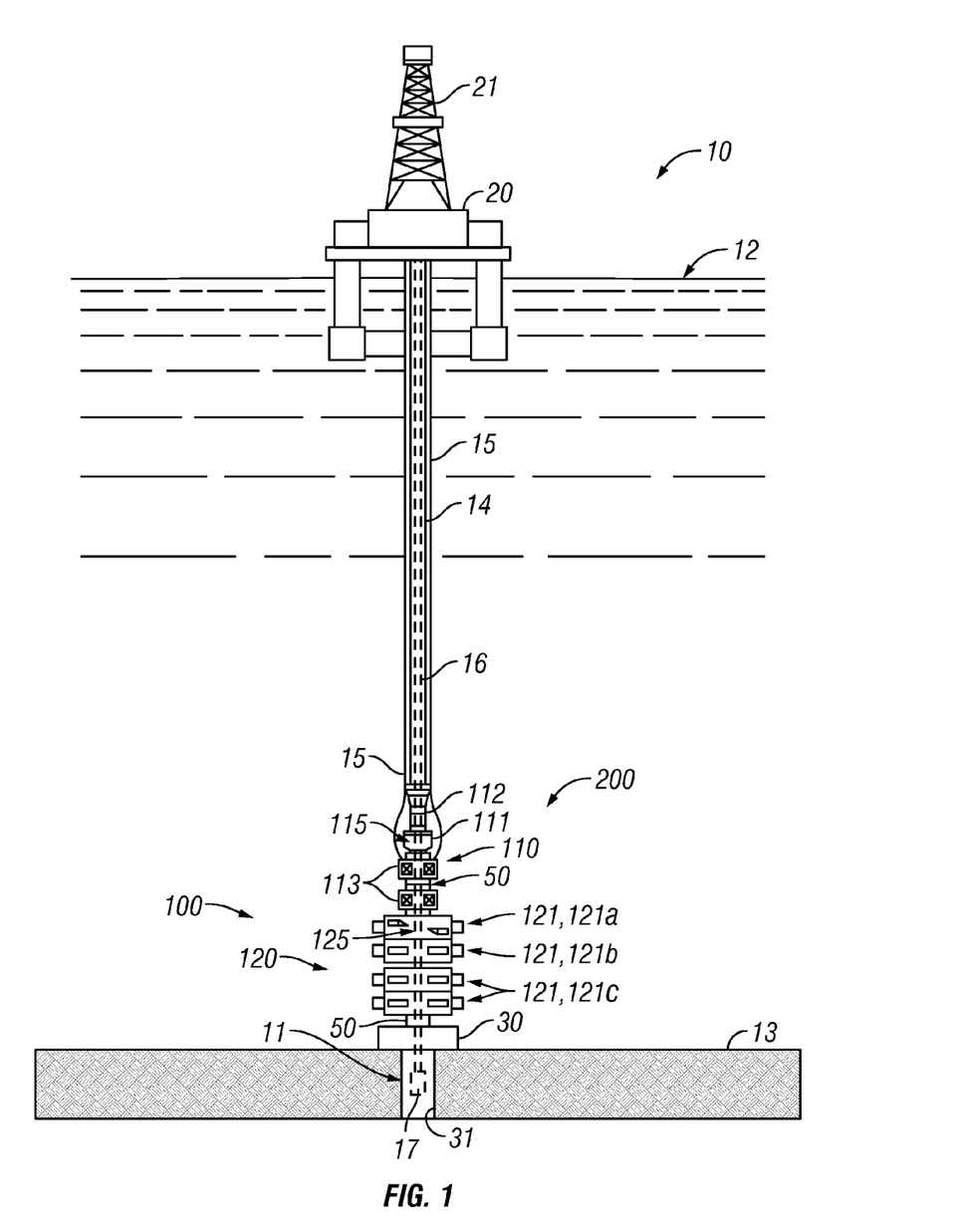
FIG. 1 shows a schematic view of an offshore system for drilling and/or producing a subterranean wellbore.

Referring now to FIG. 1, an embodiment of an offshore system 10 for drilling and/or producing a wellbore 11 is shown. In this embodiment, the system 10 includes an offshore vessel or platform 20 at the sea surface 12 and a subsea BOP stack assembly 100 mounted to a wellhead 30 at the sea floor 13. The platform 20 is equipped with a derrick 21 that supports a hoist (not shown). A tubular drilling riser 14 extends from the platform 20 to the BOP stack assembly 100. The riser 14 returns drilling fluid or mud to the platform 20 during drilling operations. One or more hydraulic conduits 15 extend along the outside of the riser 14 from the platform 20 to the BOP stack assembly 100. The one or more hydraulic conduits 15 supply pressurized hydraulic fluid to the assembly 100. Casing 31 extends from the wellhead 30 into the subterranean wellbore 11.

Downhole operations are carried out by a tubular string 16 (e.g., drill string, tubing string, coiled tubing, etc.) that is supported by the derrick 21 and extends from the platform 20 through the riser 14, through the BOP stack assembly 100 and into the wellbore 11. A downhole tool 17 is connected to the lower end of the tubular string 16. In general, the downhole tool 17 may comprise any suitable downhole tools for drilling, completing, evaluating and/or producing the wellbore 11 including, without limitation, drill bits, packers, cementing tools, casing or tubing running tools, testing equipment, perforating guns, and the like. During downhole operations, the string 16, and hence the tool 17 coupled thereto, may move axially, radially and/or rotationally relative to the riser 14 and the BOP stack assembly 100.

Figure 2:
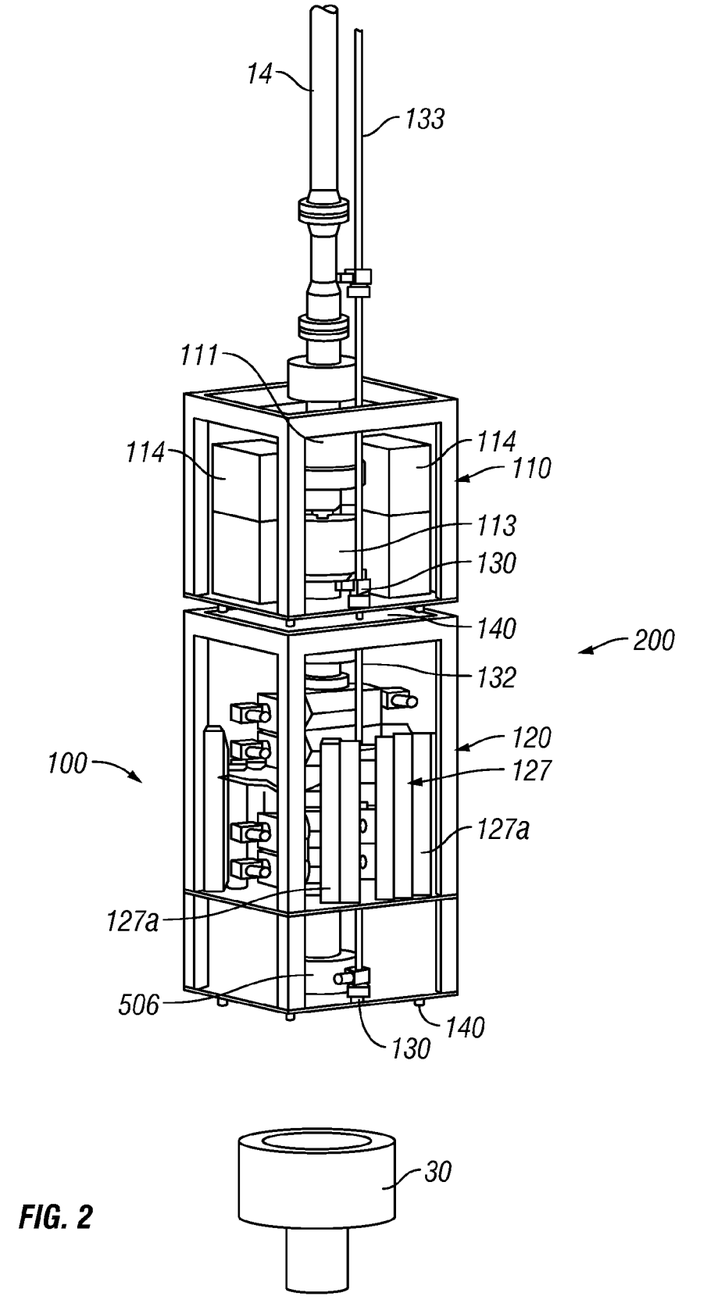
FIG. 2 shows a perspective view of a subsea BOP stack assembly and measurement system.

Referring now to FIGS. 1-2, the BOP stack assembly 100 is mounted to the wellhead 30 and is designed and configured to control and seal the wellbore 11, thereby containing the hydrocarbon fluids (i.e., liquids and gases) therein. In this embodiment, the BOP stack assembly 100 comprises a lower marine riser package (LMRP) 110 and a BOP or BOP stack 120.

The BOP stack 120 is releasably secured to the wellhead 30 as well as the LMRP 110 and the LMRP 110 is releasably secured to the BOP stack 403 and the riser 14. In this embodiment, the connections between the wellhead 30, the BOP stack 120 and the LMRP 110 include hydraulically actuated, mechanical wellhead-type connections 50. In general, the connections 50 may comprise any suitable releasable wellhead-type mechanical connection such as the DWHC or HC profile subsea wellhead system available from Cameron® International Corporation of Houston, Tex., or any other such wellhead profile available from several subsea wellhead manufacturers. Typically, such hydraulically actuated, mechanical wellhead-type connections (e.g., the connections 50) include an upward-facing male connector or "hub" that is received by and releasably engages a downward-facing mating female connector or receptacle 50b. In this embodiment, the connection between LMRP 110 and the riser 14 is a flange connection that is not remotely controlled, whereas the connections 50 may be remotely, hydraulically controlled.

Referring still to FIGS. 1-2, the LMRP 110 includes a riser flex joint 111, a riser adapter 112, an annular BOP 113 and a pair of redundant control units or pods 114. A flow bore 115 extends through the LMRP 110 from the riser 14 at the upper end of the LMRP 110 to the connection 50 at the lower end of the LMRP 110. The riser adapter 112 extends upward from the flex joint 111 and is coupled to the lower end of the riser 14. The flex joint 111 allows the riser adapter 112 and the riser 14 connected thereto to deflect angularly relative to the LMRP 110 while wellbore fluids flow from the wellbore 11 through the BOP stack assembly 100 into the riser 14. The annular BOP 113 comprises an annular elastomeric sealing element that is mechanically squeezed radially inward to seal on a tubular extending through the LMRP 110 (e.g., the string 16, casing, drillpipe, drill collar, etc.) or seal off the flow bore 115. Thus, the annular BOP 113 has the ability to seal on a variety of pipe sizes and/or profiles, as well as perform a complete shut-off ("CSO") to seal the flow bore 115 when no tubular is extending therethrough.

In this embodiment, the BOP stack 120 comprises an annular BOP 113 as previously described, choke/kill valves 131 and choke/kill lines 132. The choke/kill line connections 130 connect the female choke/kill connectors of the LMRP 110 with the male choke/kill adapters of the BOP stack 120, thereby placing the choke/kill connectors of the LMRP 110 in fluid communication with the choke lines 132 of the BOP stack 120. A main bore 125 extends through the BOP stack 120. In addition, the BOP stack 120 includes a plurality of axially stacked ram BOPs 121. Each ram BOP 121 includes a pair of opposed rams and a pair of actuators 126 that actuate and drive the matching rams. In the illustrated embodiment, the BOP stack 120 includes four ram BOPs 121—an upper ram BOP 121 including opposed blind shear rams or blades 121a for severing the tubular string 16 and sealing off the wellbore 11 from the riser 14, and the three lower ram BOPs 121 including the opposed pipe rams 121c for engaging the string 16 and sealing the annulus around the tubular string 16. In other embodiments, the BOP stack 120 may include a different number of rams, different types of rams, one or more annular BOPs or combinations thereof. As will be described in more detail below, the control pods 114 operate the valves 131, the ram BOPs 121 and the annular BOPs 113 of the LMRP 110 and the BOP stack 120.

The opposed rams 121a, c are located in cavities that intersect the main bore 125 and support the rams 121a, c as they move into and out of the main bore 125. Each set of rams 121a, c is actuated and transitioned between an open position and a closed position by matching actuators 126. In particular, each actuator 126 hydraulically moves a piston within a cylinder to move a connecting rod coupled to one ram 121a, c. In the open positions, the rams 121a, c are radially withdrawn from the main bore 125. However, in the closed positions, the rams 121a, c are radially advanced into the main bore 125 to close off and seal the main bore 125 and/or the annulus around the tubular string 16. The main bore 125 is substantially coaxially aligned with the flow bore 115 of the LMRP 110, and is in fluid communication with the flow bore 115 when the rams 121a, c are open.

As shown in FIG. 2, the BOP stack 120 also includes a set or bank 127 of hydraulic accumulators 127a mounted on the BOP stack 120. While the primary hydraulic pressure supply is provided by the hydraulic conduits 15 extending along the riser 14, the accumulator bank 127 may be used to support operation of the rams 121a, c (i.e., supply hydraulic pressure to the actuators 126 that drive the rams 121a, c of the stack 120), the choke/kill valves 131, the connector 50b of the BOP stack 120 and the choke/kill connectors 130 of the BOP stack 120. As will be explained in more detail below, the accumulator bank 127 may serve as a backup means to provide hydraulic power to operate the rams 121a, c, the valves 131, the connector 50b, and the connectors 130 of the BOP stack 120.

Although the control pods 114 may be used to operate the BOPs 121 and the choke/kill valves 131 of the BOP stack 120 in this embodiment, in other embodiments, the BOPs 121 and the choke/kill valves 131 may also be operated by one or more subsea remotely operated vehicles ("ROVs").

As previously described, in this embodiment, the BOP stack 120 includes one annular BOP 113 and four sets of rams (one set of shear rams 121a, and three sets of pipe rams 121b, c). However, in other embodiments, the BOP stack 120 may include different numbers of rams, different types of rams, different numbers of annular BOPs (e.g., annular BOP 113) or combinations thereof. Further, although the LMRP 110 is shown and described as including one annular BOP 113, in other embodiments, the LMRP (e.g., LMRP 110) may include a different number of annular BOPs (e.g., two sets of annular BOPs 113). Further, although the BOP stack 120 may be referred to as a "stack" because it contains a plurality of ram BOPs 121 in this embodiment, in other embodiments, BOP 120 may include only one ram BOP 121.

Figure 3:
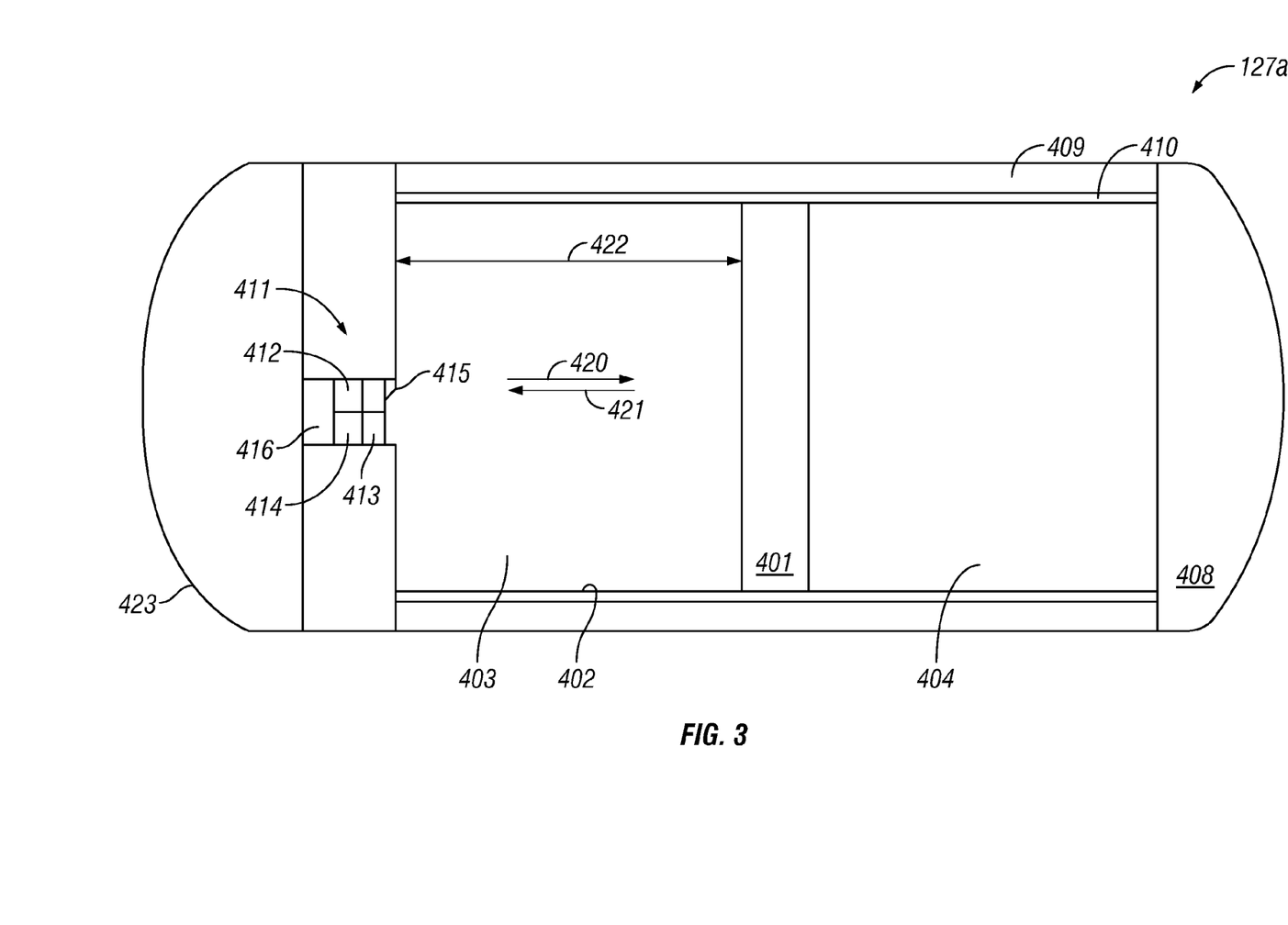
FIG. 3 shows a cross section view of an embodiment of a system for measuring the position of a movable element in a container.

Referring now to FIG. 3, a more detailed cross-sectional view is provided that illustrates a hydraulic accumulator with a measurement system. The hydraulic accumulator 127a includes an element 401 movable within the internal volume, or cavity, 402. The hydraulic accumulator 127a body is composed of an outer layer and an inner layer. The outer layer 409 of the accumulator 127a may include a metal, metal alloy and/or composite material (e.g., carbon fiber reinforced plastic). Composite materials are lighter than steel counterparts and possess high strength and stiffness, providing high performance in deep water, high pressure applications. The inner layer 410 of the accumulators 127a may include a metal and/or metal alloy.

In the embodiment in FIG. 3, the movable element 401 is a piston separating a hydraulic fluid 403 from a gas 404 stored in the internal volumes of the accumulators 127a. It should be appreciated by those of ordinary skill in the art that the movable element could be any device movable in an internal volume of a container that is capable of separating fluids. The piston 401 may include a metal, metal alloy, plastic, or rubber.

In the embodiment in FIG. 3, the accumulator includes a measurement system which includes a sensor module 411 and a control connector 416 recessed in a housing 417. The sensor module 411 and control connector 416 are installed in the fluid end of the accumulator 127a and configured to control the ultrasonic transducer 412 to emit ultrasonic pulses toward the piston 401. In the illustrated embodiment, the fluid end of the accumulator 127a includes a recess configured to receive the sensor module 411 and control connector 416. The sensor module 411 includes an ultrasonic transducer 412, a temperature sensing device 414 a pressure sensing device 413 and a transducer window 415. In certain embodiments, the temperature sensing device 414 may be a 4-wire resistance temperature detector. In certain embodiments, the transducer 412 may be of a model of an ultrasound transducer module manufactured by Cameron International Corporation.

In the illustrated embodiment, the temperature sensing device 414 and the pressure sensing device 413 are integrated within the ultrasonic transducer housing 417, with the pressure sensing device being in contact with the hydraulic fluid in order to measure the pressure of the fluid in the cavity 402. In alternative embodiments, the temperature sensing device 414 and the pressure sensing device 413 can be embedded on the ultrasonic transducer 412 or located outside of the sensor housing 417.

In the present embodiment, an opening 418 is also provided and may extend through the head of the accumulator 127*a* to allow for the passage of wiring between the sensor module 411 and control connector 416.

The sensor module 411 and control connector 416 may be secured within the recess 419 using any suitable mechanism. For instance, in one embodiment, both the recess 409 and the housing 417 may be threaded and generally cylindrical in shape. Accordingly, the sensor module 411 and control connector 416 may be installed in the recess 417 by simply rotating the housing 417 into the recess 419, thus allowing the respective threads to engage one another. In other embodiments, the sensor module 411 and control connector 416 may be secured in the recess 419 using an adhesive, connectors, or any other suitable technique. Overall, this provides for straightforward installation of the sensor module 411 and control connector 416 without requiring significant and/or complex redesign of existing subsea equipment.

To monitor the linear position of the piston 401 during operation, the ultrasonic position sensor module 411 may intermittently transmit an ultrasonic pulse 420. The pulse 420 may originate from the ultrasonic transducer 412 located in the sensor module 411, and propagate through the window 415 and into the cavity 402, which may be filled with pressurized hydraulic fluid 403. The window 415 may include a high compressive strength plastic material having acoustic impedance properties that are similar to liquid. This allows for the transmitted pulse 420 to leave the sensor housing 417 while experiencing relatively little acoustic impedance. By way of example only, the window 415 may formed using a polyetherimide material, such as Vespel™, available from E.I. du Pont de Nemours and Company of Wilmington, Del., such as ULTEM™, available from SABIC of Saudi Arabia, organic polymer thermoplastic materials, such as polyether ether ketone (PEEK), or a polyimide-based plastic. The housing 417 may be manufactured using a metal material, such as steel or titanium, or may be formed using one of the aforementioned plastic materials, or using a combination of metal and plastic materials. In one embodiment, the housing 417 may be made of Inconel superalloy, such as Inconel 625.

After propagating through the window 415, the pulse 420 then travels the distance 422 between the head of the accumulator 127*a* and the piston 401 through the hydraulic fluid 403. Upon impacting the piston 401, the pulse 420 is reflected in the form of a corresponding echo 421. The transducer 412 receives the echo 421 as it propagates back toward the sensor module 411 through the hydraulic fluid 403 and the window 415.

The transducer 412 may operate at any suitable frequency, such as between approximately 200 kilohertz and 5.0 megahertz. In one embodiment, the transducer 412 is configured to operate at a frequency of approximately 3.5 megahertz. Further, though not expressly shown in FIG. 3, the sensor module 411 and control connector 416 may include wiring that may be routed through the opening 418. This wiring may represent the wiring that provides for communication between the sensor module 411 and control connector 416.

While the recess 419 is shown in FIG. 3 as having a width (e.g., a diameter in the case of a circular recess) that is greater than that of the opening 418, in one embodiment, the recess 419 may be an opening that extends all the way through the end cap 423. That is, the opening 418 and the recess 419 may have the same width. In such an embodiment, the sensor housing 417 may be configured to extend through the end cap 423. Also, in such an embodiment, wiring from the sensor module 411 and control connector 416, including the ultrasonic transducer 412, pressure sensing device 417 and/or the temperature sensing device 414 may form a connector coupled to the housing 417, wherein the connector is configured to electronically connect wiring within the sensor module 411 and the control connector 416. For instance, such a connector may be accessible from outside the accumulator and may be coupled to control connector 416 using one or more suitable cables. This embodiment also allows for the sensor and control connectors to be installed from the outside of the accumulator, which obviates the need for any disassembly of the end cap 423 from the body of the accumulator during installation. For instance, where the recess 419 extends all the way through the end cap 423 and includes threads that engage corresponding threads on the sensor module 411 and control connector 416, the sensor module 411 and control connector 416 may be installed from the outside by rotating the sensor module 411 and control connector 416 into the recess 419 from the outside of the end cap 423 until the threads securely engage one another.

The control connector 416 may obtain or otherwise determine several parameters which are used to compute the path length along which the ultrasonic pulse 420 traveled prior to being reflected. This path length may correspond to the distance 422, which may enable an operator to determine the linear position of a particular device, such as the piston 401. The parameters obtained and/or determined by the control connector 416 include a computed velocity of sound (VOS) through a fluid as a function of temperature and pressure, a delay time, and a signal path transit time. For example, the temperature parameter (e.g., the temperature within the cavity 402) may be measured using the temperature sensing device 414. The pressure parameter (e.g., the pressure within the cavity 402) may be provided to the control connector 416 as an expected pressure value or, in other embodiments, may be measured pressure information provided to the control connector 416 by one or more pressure sensing devices. The VOS in the fluid can be determined by the control connector 416 based on the temperature and pressure measurements made in the sensor module 411. The VOS of the fluid medium in the accumulator can be calculated according to the following formula:

$$VOS(P,T) = Water_{\%} \times Water_{VOS}(P,T) + MEG_{\%} \times MEG_{VOS}(P,T)$$

wherein VOS (P,T) represents velocity of sound in the fluid medium located in the accumulator 127*a* as a function of pressure and temperature. $Water_{\%}$ represents the percentage of water in the fluid medium. $Water_{VOS}(P,T)$ represents velocity of sound in water, which is a known quantity at known pressures and temperatures. $MEG_{\%}$ represents percentage of monoethylene glycol in the fluid medium. $MEG_{VOS}(P,T)$ represents the velocity of sound in monoethylene glycol, which is a known quantity at known pressures and temperatures. The example formula above considered a fluid medium comprising water and monoethylene glycol. Other fluid combinations commonly known in the art for use in an accumulator are also disclosed.

The delay time may represent non-fluid delays present in the signal path which, as discussed above, includes the entire path (both electrical and acoustic portions) between the control connector 416 and the monitored device. For instance, the presence of the window 415 and the wiring may introduce non-fluid delays. By subtracting out the delay time from the total transit time and dividing the result by two, the fluid transit time of the pulse 420 (or of its corresponding echo 421) may be determined. Once the velocity of the ultrasonic pulse 420 or echo 421 through the hydraulic fluid 403 and the fluid transit time are known, the path length between the head of the accumulator 127a and the piston 401 may be calculated by the control connector 416 according to the following formula, thus providing the linear position of the piston 401:

$$D = \frac{[VOS(P, T) \times t]}{2}$$

wherein D represents the distance from the head of the accumulator 127a and the piston 401. VOS (P,T) represents velocity of sound in the fluid medium located in the accumulator 127a as a function of pressure and temperature. t represents transmit time of the pulse through the fluid medium.

By knowing the linear position of the piston 401, the system can determine how much hydraulic fluid remains in the accumulator. In some embodiments, the fluid 403 need not necessarily be a liquid. For instance, the fluid 403 may include a gas or a gas mixture, such as air.

In the present example, the ultrasonic position sensor module 411 and control connector 416 are used to monitor the linear position of a piston in an accumulator of a subsea resource extraction system. Accordingly, the sensor module 411 and control connector 416 may be designed to be durable enough to withstand harsh environmental conditions often associated with subsea operation. In one embodiment, the housing 417, in which the sensor module 411 and control connector 416 are disposed, may be manufactured using titanium, stainless steel, or any other suitable type of metal, alloy, or super-alloy, and may be capable of operating at pressures of between approximately 14 pounds per square inch (PSI) to 14,000 PSI. For example, the window 415 of the sensor housing 417 may withstand loads of up to 14,000 PSI. The sensor module 411 and control connector 416 may also be capable of withstanding operating temperatures of between 0 to 100 degrees Celsius.

Figure 4:
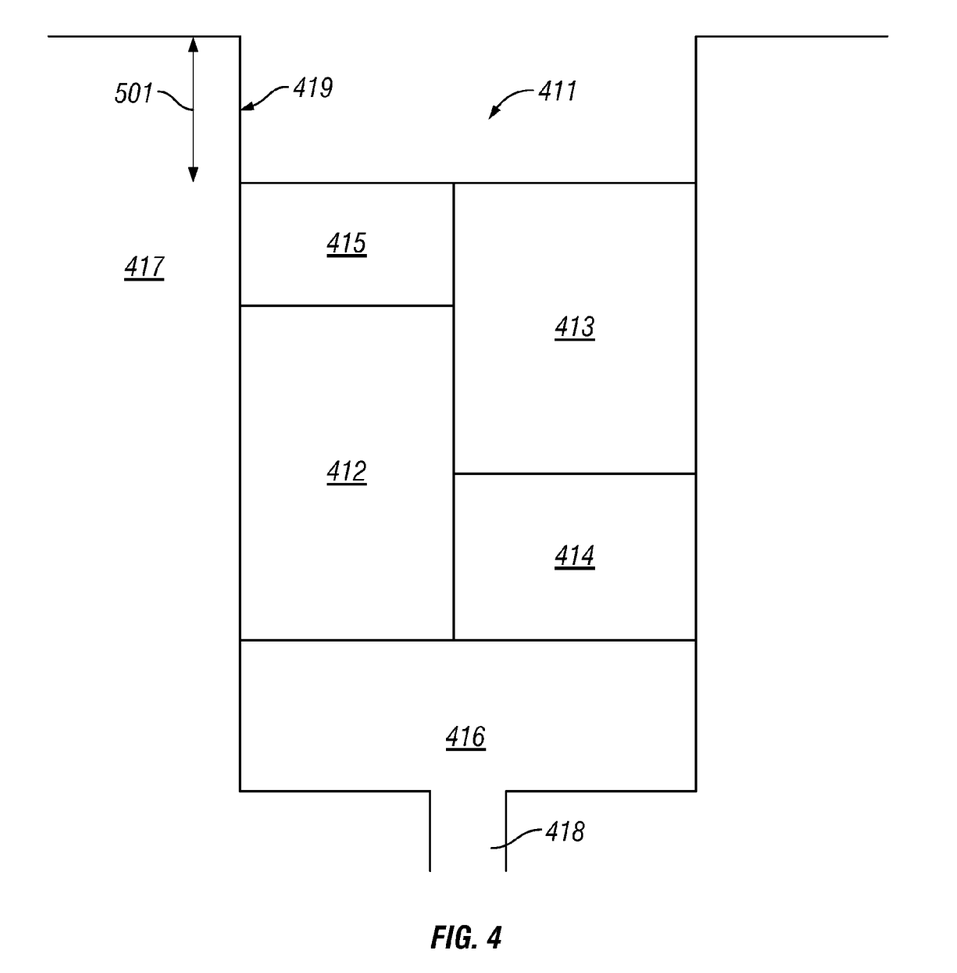
FIG. 4 shows a detail view of a measurement system for measuring the position of a movable element in a container.

As shown in FIG. 4, the sensor module 411 and control connector 416 may be recessed within the recess 419 by a distance shown by reference number 501. This distance 501 may be selected based at least partially upon certain properties of the window 415, such as thickness and sound velocity characteristics, to compensate for signal reverberation within the medium of the window 415. This reverberation is due to resonating properties of the window 415. For example, when the ultrasonic pulse 420 is transmitted from the sensor module 411, a portion of the signal 420 may reverberate within the window 415 before dissipating. The amount of time that it takes for this reverberation to dissipate may constitute what is sometimes referred to as a signal dead band. If an echo (e.g., 421) arrives at the sensor module 411 within this signal dead band, the sensor module 411 may be unable to acquire an accurate measurement due to interference from the ongoing signal reverberation within the window 415. This is generally most problematic when the target device, here the piston 401, is very close to the accumulator 127a head, such that the elapsed time for the echo 421 to return to the sensor module 411 and control connector 416 falls within the dead band. Accordingly, recessing the sensor module 411 by a distance 501 within the recess 419 may compensate for the dead band effects, thus allowing the sensor module 411 to accurately acquire measurements for generally any position of the piston 401 within the accumulator.

The distance 501 may be selected as a function of the thickness of the window and its resonance properties. For instance, a plastic material, such as VESPEL®, ULTEM™ or PEEK may have resonating properties in which an ultrasonic signal reverberates within the window 415 for approximately two round trips before dissipating. Thus, in this example, the goal in selecting the distance 501 is that the earliest time at which an echo 421 reflected from the piston 401 returns to the sensor is outside of the signal dead band time, with the most extreme case being when the piston 401 is in the open position. Additionally, it should be noted that the plastic materials discussed above generally have lower resonating properties when compared to that of certain other materials, particularly metals such as steel. By comparison, in a sensor where the ultrasonic pulse 420 is transmitted through a metal material, like steel, the ultrasonic signal 420 may reverberate for approximately ten or more round trips within the steel before dissipating.

As discussed above with reference to FIG. 3, the ultrasonic position sensor module 411 includes a transducer 412. One embodiment of the transducer 412 is shown in more detail in FIGS. 5-6, which show assembled and exploded perspective views, respectively, of the transducer 412.

Figure 5:
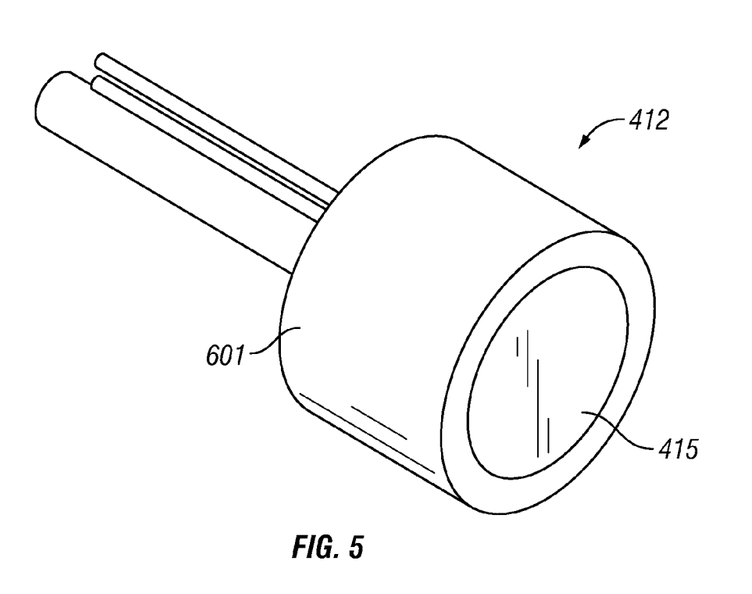
FIG. 5 shows an exploded view of an embodiment of a transducer.
Figure 6:
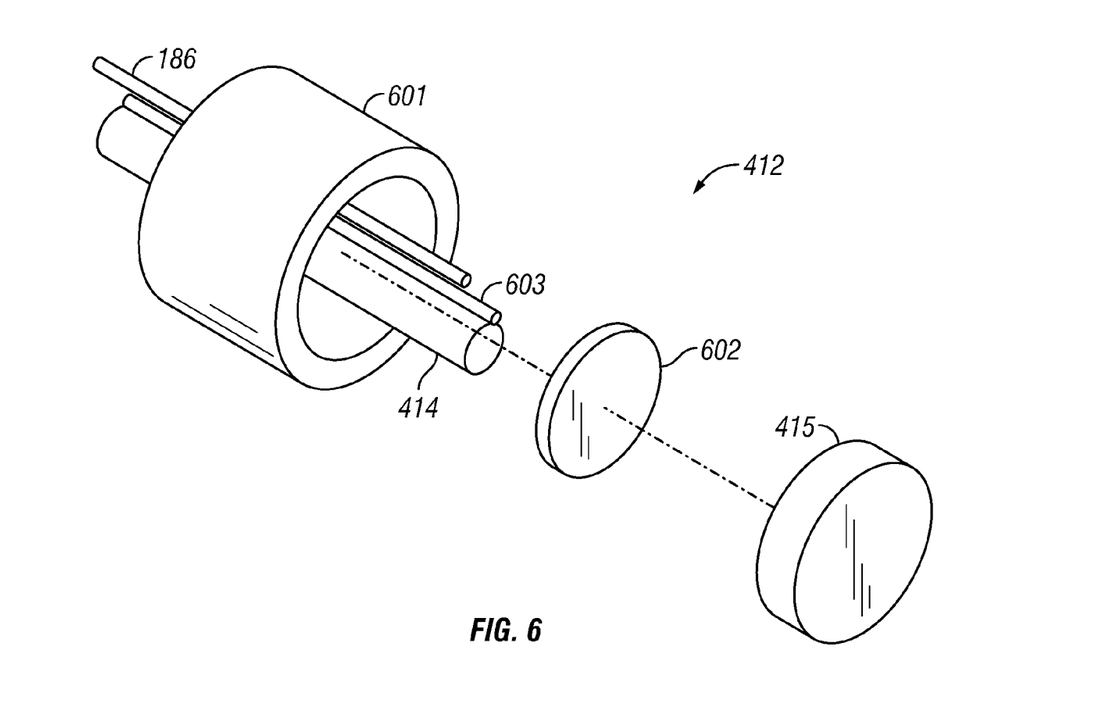
FIG. 6 shows another exploded view of an embodiment of a transducer.

The transducer 412 includes the above-described window 415, as well as a casing 601, piezoelectric material 602, positive lead 603, negative lead 604. The transducer 412 also includes the above-described temperature sensing device 414. As best shown in FIG. 5, the positive lead 603, negative lead 604, and temperature sensing device 414 extend outward from the rear end (e.g., the end opposite the window 415) of the transducer 412. When assembled within a device, such as the head of an accumulator, such as accumulator 127a, portions of the positive lead 603, negative lead 604, and temperature sensing device 414 may extend through the opening 418 (FIG. 4). The casing 601 generally encloses the components of the transducer 412 and may be designed to fit within the sensor housing 417, as shown in FIG. 4. In one embodiment, the casing 601 may be formed using the same high compressive strength plastic material as the window 415, such as ULTEM™, PEEK, or VESPEL®. In other embodiments, the casing 601 may be formed using a metal material, such as steel, titanium, or alloys thereof. The piezoelectric material 602 may be formed using a crystal or ceramic material. For example, in one embodiment, the piezoelectric material 602 may include lead zirconate titanate (PZT). In another embodiment, the piezoelectric material 602 may include lead metaniobate.

Figure 7:
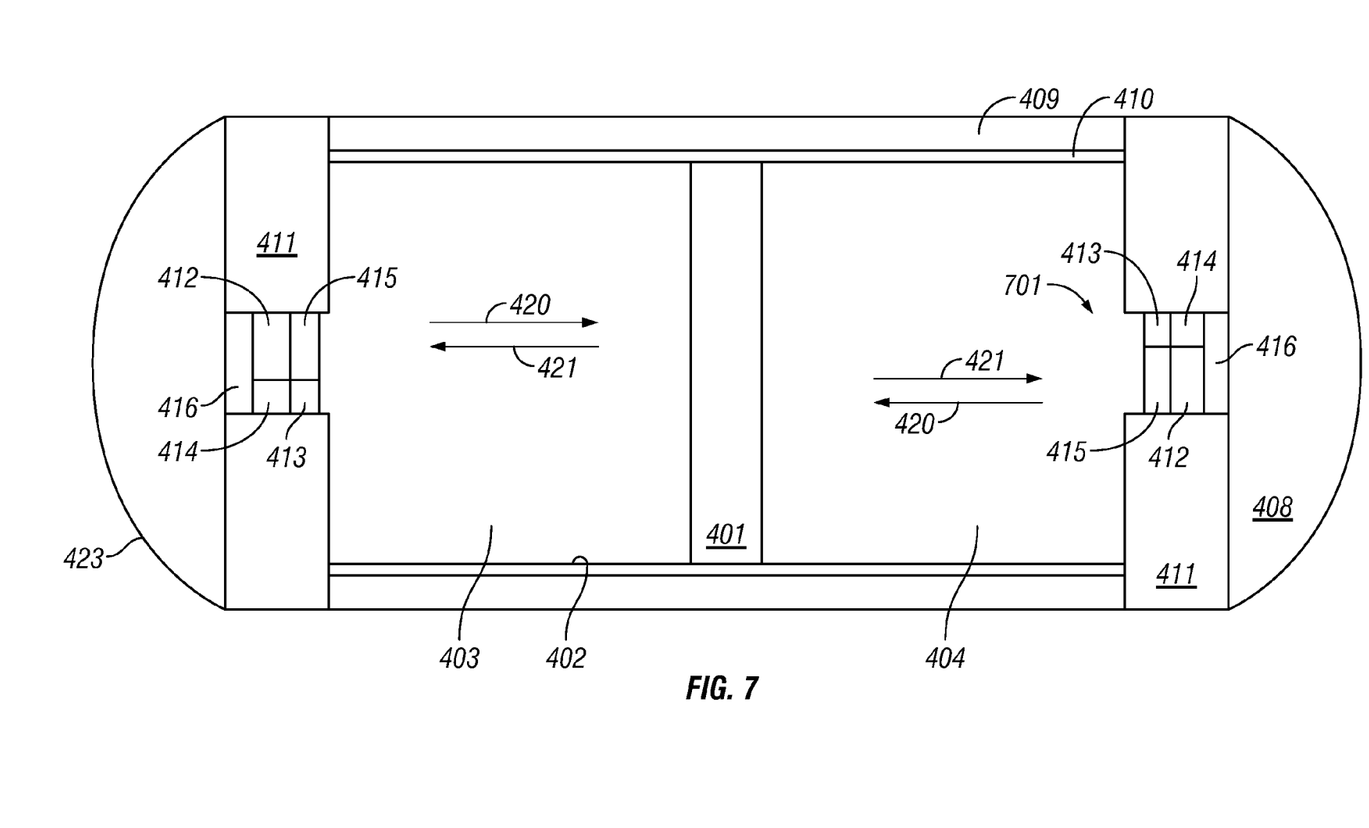
FIG. 7 shows a cross section view of an embodiment of a system for measuring the position of a movable element in a container including ultrasonic transducers on the fluid and gas sides of the accumulator.

FIG. 7 shows another illustrative embodiment of the accumulator measurement system, with another ultrasonic transducer 701 installed in the gas side 404 of the accumulator 127a. In this embodiment, the ultrasonic transducer in the gas end is a lower frequency transducer than the ultrasonic transducer of the fluid end (e.g., 200 kilohertz). Such an embodiment provides for redundancy in the event the fluid-side ultrasonic transducer malfunctions. In addition, providing a gas-side ultrasonic transducer allows for accurate piston position determination from the gas side in the event of foaming in the liquid side, which can present noise in the liquid-side measurements reducing the accuracy of the measurements.

The ultrasonic position sensing system and techniques described herein may provide position information that is substantially as accurate as position information obtained using other existing solutions, such as position monitoring using LVDTs or other electromechanical position sensors. However, as discussed above, the ultrasonic position sensing system integrates much more easily with existing subsea components and does not require substantial and complex redesign of existing equipment. Further, as the ultrasonic position sensors described herein are generally not subject to common-mode failure mechanisms, as is the case with some electromechanical position sensors, the position information obtained by the ultrasonic position sensing system may better maintain its accuracy over time.

While the examples described above have focused on the use of an ultrasonic position sensor for monitoring the position of a ram of a blowout preventer, it should be appreciated the above-described techniques may be applicable to generally any device or component of a system that moves, such as in response to actuation. For example, in the context of the oilfield industry, other types of components having linearly actuated devices that may be monitored using the ultrasonic ranging techniques described herein include blowout preventer gate valves, wellhead connectors, a lower marine riser package connector, blowout preventer choke and kill valves and connectors, subsea tree valves, manifold valves, process separation valves, process compression valves, and pressure control valves, to name but a few. Additionally, as discussed above, components that move non-linearly may also be monitored using the position sensing techniques described above.

Although the present invention has been described with respect to specific details, it is not intended that such details should be regarded as limitations on the scope of the invention, except to the extent that they are included in the accompanying claims.

What is claimed is:

1. A measurement system comprising:
   an accumulator including an element movable within an internal volume of the accumulator and an end cap with a recess formed within the internal volume of the accumulator;
   a sensor module positioned within the recess of the end cap and comprising:
      an ultrasonic transducer configured to transmit an ultrasonic signal through a fluid medium in the internal volume toward a surface of the movable element;
      a pressure sensor configured to measure the pressure of the fluid medium; and
      a temperature sensor configured to measure the temperature of the fluid medium; and
   a controller positioned within the recess of the end cap and coupled to the sensor module and configured to provide hardware and software functions to measure transit time of the ultrasonic signal through the accumulator to determine the location of the movable element within the accumulator.

2. The system of claim 1, wherein the controller hardware and software functions are configured to measure and combine the transit time of the ultrasonic signal across the fluid medium with a computed velocity of sound as a function of the temperature and pressure of the fluid medium.

3. The system of claim 1, wherein the location of the movable element within the accumulator is indicative of remaining volume of the fluid medium within the internal volume of the accumulator.

4. The system of claim 1, the controller further comprising electronics connected with and configured to communicate with the ultrasonic transducer, pressure sensor, and temperature sensor.

5. The system of claim 1, wherein the recess of the end cap further comprises a transducer window positioned between the ultrasonic transducer and the surface of the piston.

6. The system of claim 5, wherein the transducer window comprises at least one of a polyetherimide, an organic thermoplastic polymer, and a polyimide-based plastic.

7. The system of claim 1, wherein the temperature sensor is a resistance temperature detector.

8. The system of claim 1, wherein the movable element includes a piston movable within an internal volume of the accumulator.

9. The system of claim 1, further comprising a second sensor module and a second controller.

10. The system of claim 1, wherein the movable element divides the internal volume of the accumulator into a gas side and a liquid side.

11. The system of claim 1, wherein the sensor module and controller are located on a fluid side within the accumulator with respect to the movable element.

12. The system of claim 1, wherein the sensor module and controller are located on a gas side within the accumulator with respect to the movable element.

13. A subsea blowout preventer stack comprising:
   a blowout preventer;
   a subsea hydraulic accumulator configured to provide hydraulic fluid to power the blowout preventer, the accumulator comprising an internal volume with a gas side and a fluid side separated by a piston moveable within the accumulator internal volume and an end cap with a recess formed within the internal volume of the accumulator; and
   a measurement system comprising:
      a sensor module positioned within the recess of the end cap and comprising:
         an ultrasonic transducer facing the piston and configured to transmit an ultrasonic signal through a fluid medium in the accumulator internal volume toward a surface of the piston;
         a pressure sensor configured to measure the pressure of the fluid medium;
         a temperature sensor configured to measure the temperature of the fluid medium; and
      a controller positioned within the recess of the end cap and coupled to the sensor module, capable of providing hardware and software functions to measure transit time of the ultrasonic signal through the accumulator to determine the location of the movable element within the accumulator; and
      wherein the location of the piston within the accumulator is indicative of remaining volume of the fluid medium within the internal volume of the accumulator.

14. The subsea blowout preventer stack of claim 13, wherein the recess of the end cap further comprises a transducer window positioned between the ultrasonic transducer and the surface of the piston.

15. The subsea blowout preventer stack of claim 14, wherein the transducer window comprises at least one of a polyetherimide, an organic thermoplastic polymer, and a polyimide-based plastic.

16. The subsea blowout preventer stack of claim 13, wherein the temperature sensor is a resistance temperature detector.

17. The subsea blowout preventer stack of claim 13, wherein the sensor module and controller are located on a fluid side within the accumulator with respect to the movable element.

18. The subsea blowout preventer stack of claim 17, further comprising another sensor module and controller located on a gas side within the accumulator with respect to the movable element.

* * * * *